United States Patent [19]

Kawakami et al.

[11] 4,036,901
[45] July 19, 1977

[54] PROCESS FOR PRODUCING STYRENE

[75] Inventors: Masato Kawakami, Yokohama; Naoki Andoh, Yokkaichi; Akira Iio, Yokkaichi; Haruo Yamanouchi, Yokkaichi, all of Japan

[73] Assignee: Japan Synthetic Rubber Co., Ltd., Tokyo, Japan

[21] Appl. No.: 625,380

[22] Filed: Oct. 24, 1975

[30] Foreign Application Priority Data

Oct. 28, 1974 Japan .................. 49-123442

[51] Int. Cl.² .................. C07C 15/00; C07C 15/10
[52] U.S. Cl. .................. 260/669 R
[58] Field of Search .................. 260/669 R, 669 QZ; 252/464, 467, 468, 469, 470

[56] References Cited

U.S. PATENT DOCUMENTS

| | | | |
|---|---|---|---|
| 2,217,865 | 10/1940 | Groll et al. | 260/669 R |
| 2,438,041 | 3/1948 | Dutcher | 260/669 R |
| 3,380,931 | 4/1968 | Ryland | 252/467 |
| 3,409,696 | 11/1968 | Minnis et al. | 260/669 R |
| 3,446,865 | 5/1969 | Roth et al. | 260/669 R |
| 3,446,869 | 5/1969 | Nolan | 260/669 R |
| 3,502,736 | 3/1970 | Sato et al. | 260/669 R |
| 3,716,545 | 2/1973 | Ripley | 260/669 R |
| 3,870,764 | 3/1975 | Cichowski et al. | 260/669 R |
| 3,900,525 | 8/1975 | Cristmann et al. | 260/669 R |
| 3,904,552 | 9/1975 | O'Hara | 252/470 |
| 3,907,919 | 9/1975 | Lo et al. | 260/669 R |
| 3,915,893 | 10/1975 | Flanigen et al. | 260/669 R |

Primary Examiner—Edward J. Meros
Assistant Examiner—Eugene T. Wheelock
Attorney, Agent, or Firm—Oblon, Fisher, Spivak, McClelland & Maier

[57] ABSTRACT

A process for producing styrene which comprises subjecting 4-vinylcyclohexene to gas phase catalytic oxidation with a molecular oxygen-containing gas, for example, air, characterized in that the oxidation is carried out by use of a catalyst composition represented by the general formula,

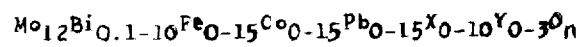

$$Mo_{12}Bi_{0.1-10}Fe_{0-15}Co_{0-15}Pb_{0-15}X_{0-10}Y_{0-3}O_n$$

wherein X is at least one element selected from the group consisting of zirconium, cadmium, niobium, and antimony; Y is at least one element selected from the group consisting of lithium, sodium, potassium, rubidium, cesium and thallium; $1 \leq Fe + Co + Pb \leq 25$; and $n$ is the number of oxygen atoms sufficient to replenish the valences of other elements. According to the above-mentioned process, styrene can be produced in a high yield.

18 Claims, No Drawings

PROCESS FOR PRODUCING STYRENE

This invention relates to a process for producing styrene in a high yield by subjecting 4-vinylcyclohexene to gas phase catalytic oxidation in the presence of a novel catalyst.

For the commercial scale production of styrene, four processes have heretofore been generally employed; (1) a process in which ethylbenzene is subjected to dehydrogenation, (2) a process in which ethylbenzene is oxidized, reduced and then dehydrated, (3) a process in which petroleum is subjected to thermal cracking, and (4) a process in which styrene is recovered from by-products. At present, however, the process (1) using ethylbenzene is most frequently used.

The process using ethylbenzene requires benzene as starting material, and hence sometimes cannot produce sufficient amounts of styrene because of the supply-demand situation of benzene. For this reason, a need has existed for a process of producing styrene from a non benzene source.

It is well known that 4-vinylcyclohexene can be prepared by dimerization of butadiene. Moreover, as the butadiene for preparation of 4-vinylcyclohexene, butadiene in an inexpensive crude $C_4$ fraction which can be obtained by the cracking of petroleum can be used without any particular purification. 4-Vinylcyclohexene has been known as one of the starting materials for the production of styrene, but has not been used hitherto, since no effective process for producing styrene from 4-vinylcyclohexene has been developed.

Various processes for the production of styrene from 4-vinylcyclohexene, heretofore have heretofore been proposed such as a process in which a platinum series metal is used as the catalyst (Japanese Patent Publication No. 8367/67), a process in which an oxide of copper, zinc, arsenic, antimony, chromium, iron or cobalt is used as the catalyst (Japanese Patent Publication No. 9168/70), and a process in which palladium hydroxide or a hydrate of palladium oxide is used as the catalyst (Japanese Patent Publication No. 9372/70 and United States Patent 3,502,736). According to the former two processes (Japanese Patent Publication Nos. 8367/67 and 9168/70), the conversion does not reach even 50%, while according to the latter process (Japanese Patent Publication No. 9372/70), both the conversion and the selectivity are high, but the space velocity is extremely low, so that the amount of 4-vinylcyclohexene capable of being treated per unit amount of the catalyst is small. Thus, every one of the abovementioned processes has not been an industrially satisfactory process for producing styrene.

Generally, when a dehydrogenation reaction is adopted, as in the production of butadiene from butane and butene or in the production of styrene from ethylbenzene, for example, not only the selectivity but also the conversion become low, and a system for regeneration of catalyst should necessarily be employed. Such a process, therefore, is not desirable. On the other hand, when an oxidative dehydrogenation reaction is used, the step in which the product is separated is complex which results in high equipment costs, and the selectivity is sometimes lowered. Accordingly, such a process is not desirable either.

With an aim to sufficiently utilize the merits and to overcome the disadvantages of the oxidative dehydrogenation reaction when used in a process for producing styrene from 4-vinylcyclohexene, the present inventors conducted extensive studies to find an excellent catalyst system.

An object of the present invention is to provide a novel process for producing styrene from 4-vinylcyclohexene.

Another object of the invention is to provide a process for producing styrene in a high yield from 4-vinylcyclohexene.

A further object of the invention is to provide a process for producing styrene in a high yield by oxidizing 4-vinylcyclohexene in the gas phase in the presence of a novel multi-component system catalyst.

A still further object of the invention is to minimize the amount of ethylbenzene produced as by-product in the production of styrene from 4-vinylcyclohexene.

Other objects and advantages of the invention will become apparent from the following description.

In accordance with the present invention, there is provided a process for producing styrene which comprises catalytically oxidizing 4-vinylcyclohexene in the gas phase with a molecular oxygen-containing gas in the presence of a catalyst represented by the formula,

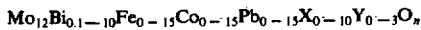

$$Mo_{12}Bi_{0.1-10}Fe_{0-15}Co_{0-15}Pb_{0-15}X_{0-15}Y_{0-10}O_n$$

wherein X is at least one element selected from the group consisting of zirconium, cadmium, niobium, and antimony; Y is at least one element selected from the group consisting of lithium, sodium, potassium, rubidium, cesium and thallium; $1 \leq Fe + Co + Pb \leq 25$; and n is the number of oxygen atoms sufficient to satisfy the valence requirements of the metallic elements.

When 4-vinylcyclohexene is subjected to oxidative dehydrogenation using a molybdenum-bismuth oxide catalyst, styrene can be obtained, but the selectivity thereof is extremely low. Such a process, therefore, cannot be utilized for industry. However, when molybdenum-bismuth is used in combination with at least one element selected from the group consisting of iron, cobalt and lead, the conversion of 4-vinylcyclohexene to styrene and the selectivity for styrene can greatly be increased. Among the said elements, the three members of iron, cobalt and lead can sufficiently be used even when employed singly, but may also be used in the form of a mixture of two or more members. Further, when a composition (A) comprising molybdenum, bismuth and at least one element selected from the group consisting of iron, cobalt and lead is incorporated with at least one element selected from the group consisting of zirconium, cadmium, niobium, and antimony, the conversion for styrene further increases. Alternatively, when the abovementioned composition (A) is incorporated with at least one element selected from the group consisting of lithium, sodium, potassium, rubidium, cesium and thallium, the selectivity for styrene further increases through the conversion for styrene scarcely varies. Both the component X element and the component Y element may effectively be incorporated simultaneously into the composition (A).

The atomic proportions of elements constituting the catalyst used in the present invention are as follows: When the atomic proportion of molybdenum is 12, that of bismuth is 0.1 to 10, preferably 0.5 to 5. If the atomic proportion of bismuth is less than 0.1, the selectivity for styrene greatly lowers, while if the said proportion is more than 10, the conversion for styrene lowers. Iron, cobalt and lead are used alone or in combination of two or more, and the respective atomic proportions are 15 or less. If the atomic proportions are more than 15, the selectivity decreases. If at least two of iron, cobalt and lead are used, then the total sum of the atomic proportions thereof is 25 or less. The total sum of the atomic proportions of iron, cobalt and lead is 1 or more. If the total sum of the atomic proportions of iron, cobalt and lead is less then both the conversion and the selectivity for styrene decreases, while if it exceeds 25, the selectivity for styrene decreases, and the selectivity for carbon oxides increases. These conditions are not desirable. When iron and cobalt are used in combination, the catalyst life is long, and hence, it is preferable. The atomic proportion of X is 0 to 10, and that of Y is 0 to 3. The addition of the X and Y components in the proportions specified above is effective to enhance the conversion and selectivity for styrene. However, the addition of the X and Y components in proportions larger than specified above is insignificant. Of the X components, Sb is particularly preferable, and of the Y components, K, Rb and Cs are particularly preferable.

Preferred embodiments of the catalyst composition of the present invention have the following formulas.

a. $Mo_{12}Bi_{0.5-5}Me_{1-15}X_{0-5}Y_{0-3}O_n$, wherein Me is iron, cobalt or lead;

b. $Mo_{12}Bi_{0.5-5}Pb_{0.1-10}Co_{0.5-15}X_{0-5}Y_{0-3}O_n$, wherein $1 \leq Pb+Co$;

c. $Mo_{12}Bi_{0.5-5}Fe_{0.1-10}Pb_{0.1-10}X_{0-5}Y_{0-3}O_n$, wherein $1 \leq Fe+Pb$;

d. $Mo_{12}Bi_{0.5-5}Fe_{1-10}Co_{0.5-15}X_{0-5}Y_{0-3}O_n$;

e. $Mo_{12}Bi_{0.5-5}Fe_{1-10}Co_{2-10}Sb_{0.1-3}Y_{0-3}O_n$;

f. $Mo_{12}Bi_1Fe_8Co_8Sb_1O_n$; and g. $Mo_{12}Bi_1Fe_8Co_8Sb_1K_{0.05}O_n$.

In all of these formulas, X, Y and n have the meanings defined above.

The process of the present invention has such features as mentioned below:

1. Styrene can be produced with a high conversion and a high selectivity in a high yield.

2. The generation of heat derived from complete combustion is inhibited because of the high selectivity of the reaction, so that the amount of gas added for dilution may be small so that it is possible to treat a high concentration starting gas.

3. Since the catalyst activity is very high, the contact time can be extremely short.

Particularly, the second and third features are extremely advantageous since the increase in equipment costs can be reduced in spite of the fact that the present process is carried out according to the aforesaid conventional oxidative dehydrogenation process.

The catalyst used in the present invention may be prepared according to any of the known catalyst preparation methods, e.g. evaporation method, dipping method or coprecipitation method. For example, the catalyst is prepared in such a manner that an aqueous solution of a suitable molybdate, e.g. an aqueous solution of ammonium molybdate, is mixed with an aqueous solution of a nitrate of alkali metal or thallium, and, if necessary, an aqueous solution of a nitrate or chloride of cobalt, lead, zirconium, cadmium, niobium, or antimony, or a suspension of an oxide powder of said element is added, and the resulting mixed solution is incorporated, if necessary, with an aqueous ferric nitrate solution, and is further mixed with a solution of a suitable bismuth salt, e.g. a nitric acid-acidified solution of bismuth nitrate, the mixed solution is evaporated to dryness over a water bath, and then the resultant is molded and calcined.

The catalyst may also be prepared by, for example, the following method: Of the starting materials, the compounds which do not precipitate or are difficult to precipitate when mixed with one another are, first of all, mixed, and if necessary, the suspension of fine powder is mixed therewith, and finally, a solution of the compounds which are easy to precipitate when mixed, is mixed therewith. This is for obtaining a catalyst composition as uniform as possible.

The compounds which may be used in the preparation of the catalyst used in the present invention include salts such as nitrates, carbonates, ammonium salts, and halides; free acids; acid anhydrides; polyacids; hydroxides; heteropolyacids; and heteropolyacid salts of the elements to be contained in the catalyst.

Concrete examples of the compounds are as follows:

Mo: Ammonium molybdate, molybdenum trioxide, molybdic acid, sodium molybdate, potassium molybdate, phosphomolybdic acid, ammonium phosphomolybdate, etc.

Bi: Bismuth nitrate, bismuth oxide, etc.

Fe: Iron nitrate, iron oxide, etc.

Co: Cobalt nitrate, cobalt oxide, cobalt hydroxide, etc.

Pb: Lead nitrate, lead oxide, etc.

Zr: Zirconium dioxide, zirconium silicate, zirconyl nitrate, zirconyl chloride, etc.

Cd: Cadmium nitrate, cadmium hydroxide, etc.

Nb: Niobium pentoxide, niobium chloride, etc.

Sb: Antimony trioxide, antimony pentoxide, antimony trichloride, antimony pentachloride, etc.

Li: Lithium hydroxide, lithium acetate, lithium carbonate, lithium chloride, etc.

Na: Sodium nitrate, sodium hydroxide, sodium carbonate, sodium chloride, etc.

Rb: Rubidium nitrate, rubidium hydroxide, rubidium carbonate, rubidium chloride, etc.

Cs: Cesium nitrate, cesium hydroxide, cesium carbonate, cesium chloride, etc.

Tl: Thallium (I) nitrate, thallium (I) chloride, etc.

The calcination of the catalyst may be carried out at 250° to 800° C. Further, the catalyst may be used together with a carrier. Suitable carriers for support of the catalyst of the invention includes known carriers such as silica, alumina, pumice, zirconium silicate, and silicon carbide.

The deposition of the catalyst on a carrier can be effected in a known manner, for example, by a method in which an aqueous solution or suspension of the catalyst composition is added to the carrier, and the resulting mixture is evaporated to dryness, or a method in which the catalyst composition is calcined into oxides, water is again added thereto to form a suspension of the oxides, a carrier is added to the suspension, and the resulting mixture is then evaporated to dryness. Besides, the catalyst can be prepared by adding a graphite powder to the calcined catalyst composition, mixing the mixture uniformly, and molding the mixture into tablets. The graphite powder is used in an amount of 0.3 to 5% by weight, preferably 0.5 to 3% by weight, based on the weight of the calcined catalyst composition.

Catalysts are used in many solid physical forms such as grains and pellets. The catalyst of this invention is suitable for use in a fixed, fluidized or moving bed reactor.

In practicing the present invention, the reaction temperature is preferably from 250° to 600° C, more preferably from 300° to 550° C. The reaction is ordinarily effected at atmospheric pressure, but may be carried out under slight pressure or slightly reduced pressure. The apparent contact time is preferably from 0.1 to 10 seconds, more preferably from 0.2 to 2 seconds.

The starting 4-vinylcyclohexene used in the present invention does not have to be of high purity, and may contain other cyclic and straight chain hydrocarbons.

As the molecular oxygen-containing gas used in the present invention, air or oxygen, for example can be employed. However, the oxygen does not necessarily have to be of high purity. Ordinarily, therefore, the use of air is economical. The oxygen is used in a proportion of preferably 0.5 to 5 moles, more preferably 1 to 3 moles, per mole of 4-vinylcyclohexene.

In additon to 4-vinylcyclohexene and oxygen, a gas which is substantially inert to the reaction, e.g. nitrogen, steam or saturated hydrocarbon, may be used as a dilution gas. The dilution gas is used preferably in a proportion of at least 0.5 mole per mole of 4-vinylcyclohexene. Among the above-mentioned dilution gases, steam is particularly preferable since it not only plays the role of increasing the yield of styrene but also has an action to persist the catalyst activity. In the present invention, however, no excessive dilution is necessary because the amount of heat generated due to the reaction is small.

The present invention is illustrated in more detail below with reference to examples, but the examples are merely by way of illustration and not by way of limitation. In the examples, the conversion of 4-vinylcyclohexene, the selectivity for styrene, the selectivity for ethylbenzene and the selectivity for carbon oxides are represented by the following equations:

Conversion of 4-vinylcyclohexene (%)
$$= \frac{\text{Moles of consumed 4-vinylcyclohexene}}{\text{Moles of supplied 4-vinylcyclohexene}} \times 100$$

Selectivity for styrene(%)
$$= \frac{\text{Moles of produced styrene}}{\text{Moles of consumed 4-vinylcyclohexene}} \times 100$$

Selectivity for ethylbenzene (%)
$$= \frac{\text{Moles of produced ethylbenzene}}{\text{Moles of consumed 4-vinylcyclohexene}} \times 100$$

Selectivity for carbon oxides (%)
$$= \frac{\text{Moles of produced CO} + \text{CO}_2}{\text{Moles of consumed 4-vinylcyclohexene}} \times 100 \div 8$$

All the analyses were carried out according to gas chromatography.

EXAMPLE 1

To an aqueous solution of 6.63 g (5.35 mmol) of ammonium molybdate were aded with thorough stirring an aqueous solution of 3.10 g. (9.38 mmol) of lead nitrate and a nitric acid-acidified aqueous solution of 1.52 g (3.125 mmol) of bismuth nitrate. To this mixed solution after sufficient stirring was then added 25 g of a silicon carbide carrier having a grain diameter of 3 mm, and the resulting mixture was evaporated to dryness with occasional stirring on a water bath. The thus dried mixture was transferred to a crucible and then calcined in a muffle furnace at 500° C for 6 hours to prepare a catalyst. The metal atomic ratio of effective components in the catalyst was Mo : Bi : Pb $\approx$ 12 : 1 : 3.

5.5 Milliliters of the thus prepared catalyst was charged into a glass reactor of 20 mm in inner diameter, and a starting gas comprising 4-vinylcyclohexene (7.0 mole %), air (52.6 mole %) and steam (40.4 mole %) was passed over the catalyst at a reaction temperature of 450° C and a space velocity of 4,800 hr $^{-1}$. As a result, the conversion of 4-vinylcyclohexene was 88.3%, the selectivity for styrene was 82.6%, the selectivity for ethylbenzene was 11.7%, and the selectivity of complete oxidation product was 3.1%.

EXAMPLES 2, 3 and 14

A catalyst was prepared in the same manner as in Example 1, except that the lead nitrate was replaced by each of ferric nitrate and cobalt nitrate. Using the thus prepared catalyst, styrene was produced from 4-vinylcyclohexene under the same reaction conditions as in Example 1. The results obtained were as shown in Table 1.

EXAMPLE 4

Preparation of catalyst according to oxide deposition process

To an aqueous solution of 19.9 g of ammonium molybdate were added an aqueous solution of 9.3 g of lead nitrate and a dilute nitric acid solution of 4.5 g of bismuth nitrate. The resulting suspension was evaporated to dryness, and the resultant was heated at 300° C for 4 hours and then ground to prepare a catalyst powder. 7.5 Grams of this catalyst powder was suspended in 50 ml of water, and then 30 g of a silicon carbide carrier of 3 mm in grain diameter was added to the suspension. The resulting mixture was evaporated to dryness with stirring over a water bath to deposit the catalyst powder onto the carrier, and the resultant was calcined at 500° C for 5 hours to prepare a catalyst. The metal atomic ratio of effective components in the catalyst was Mo : Bi : Pb $\approx$ 12 : 1 : 3, and the proportion of the catalyst powder deposited on the carrier was about 20% in terms of oxide. Using 5.5 ml of the thus prepared catalyst, the same reaction as in Example 1 was effected. The results obtained were as shown in Table 1.

EXAMPLES 5 - 8

A catalyst was prepared in the same manner as in Example 4 by use of each of lead nitrate and ferric nitrate in place thereof. Using the thus prepared catalyst, the same reaction as in Example 1 was effected. The results obtained were as shown in Table 1.

COMPARATIVE EXAMPLE 1

A catalyst was prepared in the same manner as in Example 1, except that the lead nitrate was not used. Using the thus prepared catalyst, the same reaction as in Example 1 was effected. The results obtained were as shown in Table 1.

COMPARATIVE EXAMPLES 2 - 4

A catalyst was prepared in the same manner as in Examples 1 - 3, except that the bismuth nitrate was not used. Using the thus prepared catalyst, the same reaction as in Example 1 was effected. The results obtained were as shown in Table 1.

When the results of Examples 1 to 8 are compared with those of Comparative Examples 1 to 4, the effectiveness of catalysts of the system molybdenumbismuth-Me (where Me is iron, cobalt or load) is apparent.

EXAMPLES 9 AND 10 AND COMPARATIVE EXAMPLE 5

A catalyst was prepared in the same manner as in Example 6, except that the amounts of the ferric nitrate and the bismuth were varied. Using the thus prepared catalyst, the same reaction as in Example 1 was effected. The results obtained were as shown in Table 1.

When the results of Comparative Examples 3 and 5 are compared with those of Examples 6, 9 and 10, the range of preferable proportion of bismuth nitrate is apparent.

EXAMPLES 11 - 13

A catalyst was prepared in the same manner as in Example 1, except that the lead nitrate was used in combination with each of cobalt nitrate and ferric nitrate or the lead nitrate was replaced by a combination of cobalt nitrate with ferric nitrate. Using the thus prepared catalyst, the same reaction as in Example 1 was effected. The results obtained were as shown in Table 1.

EXAMPLES 15 - 19

A catalyst was prepared in the same manner as in Example 2, except that prior to addition of the ferric nitrate, there was added each of zirconium oxide, cadmium nitrate, niobium pentoxide, and antimony trioxide. Using the thus prepared catalyst, the same reaction as in Example 1 was effected. The results obtained were as shown in Table 1.

COMPARATIVE EXAMPLES 6 - 9

A catalyst was prepared in the same manner as in each of Examples 15 to 19, except that the bismuth nitrate and the ferric nitrate were not used. Using the thus prepared catalyst, the same reaction as in Example 1 was effected. The results obtained were as shown in Table 1.

EXAMPLES 20 - 25

A catalyst was prepared in the same manner as in Example 12, except that prior to addition of the cobalt nitrate and the ferric nitrate, an alkali metal nitrate (a hydroxide in the case of lithium) or thallous nitrate was added to the ammonium molybdate. Using the thus prepared catalyst, the same reaction as in Example 1 was effected. The results obtained were as shown in Table 1.

EXAMPLES 26 and 27

A catalyst was prepared in the same manner as in Example 4, except that aqueous solutions of potassium nitrate, cobalt nitrate, ferric nitrate and bismuth nitrate were added in this order to the aqueous solution of ammomium molybdate without using the solution of lead nitrate. Using the thus prepared catalyst, the same reaction as in Example 1 was effected. The results obtained were as shown in Table 1.

EXAMPLE 28

To an aqueous solution of 21.2 g (17.15 mmol) of ammonium paramolybdate were added an aqueous solution of 23.3 g (80 mmol) of cobalt nitrate and then a hydrochloric acid-acidified aqueous solution of 2.28 g (10 mmol) of antimony trichloride, and the resulting mixture was sufficiently stirred. Subsequently, an aqueous solution of 32.3 g (80 mmol) of ferric nitrate and a nitric acid-acidified aqueous solution of 4.85 g (10 mmol) of bismuth nitrate were added with stirring, and the mixture was evaporated to dryness with occasional stirring on a water bath. The dried mixture was transferred to a crucible and thermally decomposed in a muffle furnace at 300° C for 5 hours, and the resulting oxide was ground in a mortar. 7.5 Grams of the thus obtained oxide powder was mixed with 30 g of a silicon carbide carrier having a grain diameter of 3 mm and 50 cc of distilled water. The resulting mixture was evaporated to dryness with stirring on a water bath, and then calcined in a muffle furnace at 700° C for 5 hours to prepare a catalyst. The metal atomic ratio of effective components in the catalyst was Mo : Bi : Fe : Co : Sb $\simeq$ 12 : 1 : 8 : 8 : 1. Using 5.5 ml of the thus prepared catalyst, the same reaction as in Example 1 was effected. The results obtained were as shown in Table 1.

EXAMPLES 29 - 35

A catalyst was prepared in the same manner as in Example 28, except that prior to addition of the cobalt nitrate, an alkali metal nitrate (a hydroxide in the case of lithium) or thallous nitrate was added. Using the thus prepared catalyst, the same reaction as in Example 1 was effected. The results obtained were as shown in Table 1.

EXAMPLE 36

A catalyst was prepared in the same manner as in Example 28, except that lead nitrate was substituted for the ferric nitrate. Using the thus prepared catalyst, the same reaction as in Example 1 was effected. The results obtained were as shown in Table 1.

EXAMPLE 37

A catalyst was prepared in the same manner as in Example 28, except that lead nitrate was substituted for the cobalt nitrate. Using the thus prepared catalyst, the same reaction was effected as in Example 1. The results obtained were as shown in Table 1.

EXAMPLE 38

A catalyst was prepared in the same manner as in Example 28, except that prior to the addition of the cobalt nitrate, lead nitrate, zirconium oxide and potassium nitrate were added and the antimony trichloride was not used. Using the thus prepared catalyst, the same reaction as in Example 1 was effected. The results obtained were as shown in Table 1.

EXAMPLE 39 AND COMPARATIVE EXAMPLE 10

A catalyst was prepared in the same manner as in Example 28, except that the amount of the cobalt nitrate was increased. Using the thus prepared catalyst, the same reaction as in Example 1 was effected. The results obtained were as shown in Table 1.

The results of Comparative Example 10 show that the conversion decreases to a great extent when the contents of iron and cobalt are too large.

COMPARATIVE EXAMPLES 11 - 13

A catalyst was prepared in the same manner as in Example 4, except that an excess of iron, lead or cobalt was added in addition to molybdenum and bismuth. Using the thus prepared catalyst, the same reaction as in Example 1 was effected. The results obtained were as shown in Table 1.

The results of Comparative Examples 11 to 13 show that in the case of a catalyst containing an excess of iron, lead or cobalt, the selectivity for styrene greatly lowers and the selectivity for ethylbenzene increases.

Table 1

|  |  | Catalyst composition | Conversion (%) | Selectivity (%) Styrene | Ethylbenzene | $CO + CO_2$ |
|---|---|---|---|---|---|---|
| Example | 1 | $Mo_{12}Bi_1Pb3$ | 88.3 | 82.6 | 11.7 | 3.1 |
|  | 2 | $Mo_{12}Bi_1Fe3$ | 81.4 | 80.4 | 14.6 | 3.3 |
|  | 3 | $Mo_{12}Bi_1Co3$ | 85.5 | 77.5 | 11.1 | 4.2 |
|  | 4* | $Mo_{12}Bi_1Pb3$ | 92.7 | 83.6 | 5.9 | 3.3 |
|  | 5* | $Mo_{12}Bi_1Pb6$ | 84.5 | 84.1 | 7.5 | 4.2 |
|  | 6* | $Mo_{12}Bi_1Fe3$ | 91.7 | 81.5 | 6.9 | 3.5 |
|  | 7* | $Mo_{12}Bi_1Fe6$ | 91.1 | 81.7 | 7.1 | 3.3 |
|  | 8* | $Mo_{12}Bi_1Fe8$ | 82.2 | 85.1 | 8.2 | 3.0 |
| Comparative Example | 1 | $Mo_{12}Bi1$ | 47.1 | 40.2 | 44.2 | 4.1 |
|  | 2 | $Mo_{12}Pb3$ | 77.8 | 28.8 | 45.3 | 4.2 |
|  | 3 | $Mo_{12}Fe3$ | 76.9 | 26.1 | 48.3 | 4.0 |
|  | 4 | $Mo_{12}Co3$ | 40.3 | 25.1 | 47.1 | 7.0 |
| Example | 9* | $Mo_{12}Bi_{0.5}Fe3$ | 83.5 | 70.5 | 20.1 | 4.8 |
|  | 10* | $Mo_{12}Bi_8Fe3$ | 85.5 | 80.3 | 7.1 | 3.5 |
| Comparative Example | 5* | $Mo_{12}Bi_{15}Fe3$ | 55.1 | 70.0 | 15.3 | 6.8 |
| Example | 11 | $Mo_{12}Bi_1Pb_3Co1$ | 90.1 | 81.5 | 10.3 | 5.1 |
|  | 12 | $Mo_{12}Bi_1Fe_3Co8$ | 91.4 | 82.5 | 7.5 | 3.5 |
|  | 13 | $Mo_{12}Bi_1Pb_3Fe1$ | 85.3 | 83.5 | 8.0 | 3.5 |
| Example | 14 | $Mo_{12}Bi_5Fe5$ | 85.1 | 78.0 | 12.1 | 4.4 |
|  | 15 | $Mo_{12}Bi_5Fe_5Zr3$ | 89.3 | 77.5 | 13.0 | 4.5 |
|  | 16 | $Mo_{12}Bi_5Fe_5Cd3$ | 88.5 | 77.5 | 14.8 | 4.0 |
|  | 17 | $Mo_{12}Bi_5Fe_5Nb3$ | 93.1 | 78.0 | 13.0 | 4.5 |
|  | 18 | $Mo_{12}Bi_5Fe_5Sb3$ | 88.3 | 81.1 | 10.3 | 4.1 |
|  | 19 | $Mo_{12}Bi_1Fe_3Sb1$ | 85.3 | 85.1 | 8.5 | 5.5 |
| Comparative Example | 6 | $Mo_{12}Zr3$ | 51.0 | 24.3 | 46.3 | 6.0 |
|  | 7 | $Mo_{12}Cd3$ | 53.3 | 26.2 | 47.3 | 5.9 |
|  | 8 | $Mo_{12}Nb3$ | 78.1 | 20.8 | 41.6 | 6.6 |
|  | 9 | $Mo_{12}Sb3$ | 21.3 | 38.1 | 43.5 | 10.9 |
| Example | 20 | $Mo_{12}Bi_1Fe_3Co_8Li0.5$ | 90.5 | 84.5 | 6.6 | 3.9 |
|  | 21 | $Mo_{12}Bi_1Fe_3Co_8Na0.2$ | 88.4 | 84.5 | 6.1 | 4.1 |
|  | 22 | $Mo_{12}Bi_1Fe_3Co_8K0.1$ | 85.0 | 85.0 | 4.5 | 4.0 |
|  | 23 | $Mo_{12}Bi_1Fe_3Co_8Rb0.1$ | 80.8 | 87.1 | 4.5 | 3.9 |
|  | 24 | $Mo_{12}Bi_1Fe_3Co_8Cs0.03$ | 78.9 | 87.5 | 4.5 | 3.5 |
|  | 25 | $Mo_{12}Bi_1Fe_3Co_8Tl0.1$ | 82.1 | 88.5 | 4.5 | 3.3 |
|  | 26* | $Mo_{12}Bi_1Fe_3Co_8K0.1$ | 73.1 | 85.1 | 4.5 | 3.6 |
|  | 27* | $Mo_{12}Bi_1Fe_8Co_8K0.1$ | 72.4 | 86.5 | 4.4 | 3.7 |
|  | 28* | $Mo_{12}Bi_1Fe_8Co_8Sb1$ | 89.5 | 85.0 | 5.2 | 4.3 |
|  | 29* | $Mo_{12}Bi_1Fe_8Co_8Sb_1Li0.5$ | 86.5 | 86.1 | 4.8 | 3.5 |
| Example | 30* | $Mo_{12}Bi_1Fe_8Co_8Sb_1Na0.2$ | 87.1 | 86.5 | 4.8 | 3.9 |
|  | 31* | $Mo_{12}Bi_1Fe_8Co_8Sb_1K0.1$ | 86.8 | 88.5 | 4.3 | 4.1 |
|  | 32* | $Mo_{12}Bi_1Fe_8Co_8Sb_1Rb0.1$ | 86.5 | 87.5 | 4.8 | 4.0 |
|  | 33* | $Mo_{12}Bi_1Fe_8Co_8Sb_1Cs0.03$ | 81.5 | 90.1 | 5.1 | 4.0 |
|  | 34* | $Mo_{12}Bi_1Fe_8Co_8Sb_1Tl0.1$ | 83.5 | 90.0 | 4.1 | 3.2 |
|  | 35* | $Mo_{12}Bi_1Fe_8Co_8Sb_1K0.05$ | 87.5 | 90.0 | 4.3 | 3.3 |
|  | 36* | $Mo_{12}Bi_1Pb_3Co_1Sb1$ | 88.5 | 85.1 | 6.8 | 4.0 |
|  | 37* | $Mo_{12}Bi_1Pb_3Fe_1Sb1$ | 85.3 | 86.1 | 5.9 | 3.5 |
|  | 38* | $Mo_{12}Bi_1Fe_3Co_8Pb_1Zr_1K0.1$ | 87.0 | 85.0 | 4.5 | 3.7 |
|  | 39* | $Mo_{12}Bi_1Fe_8Co_{12}Sb1$ | 80.5 | 86.1 | 5.3 | 3.6 |
| Comparative Example | 10* | $Mo_{12}Bi_1Fe_8Co_{20}Sb1$ | 51.0 | 72.8 | 15.1 | 5.7 |
|  | 11* | $Mo_{12}Bi_1Fe30$ | 79.5 | 45.1 | 38.1 | 13.5 |
|  | 12* | $Mo_{12}Bi_1Pb30$ | 81.5 | 40.1 | 35.1 | 15.1 |
|  | 13* | $Mo_{12}Bi_1Co30$ | 37.5 | 53.5 | 34.1 | 10.5 |

(The mark* shows the case where oxide adhesion process was adopted.)

What is claimed is:

1. A process for producing styrene by the oxidation of a 4-vinylcyclohexene, which comprises:
   contacting 4-vinylcyclohexene in the gas phase at a temperature of 250° - 600° C with a molecular oxygen-containing gas at a contact time of 0.1-10 seconds in the presence of a catalyst composition consisting essentially of:

$$Mo_{12}Bi_{0.1-10}Fe_{0-15}Co_{0-15}Pb_{0-15}X_{0-10}Y_{0-3}O_n$$

wherein X is at least one element selected from the group consisting of zirconium, cadmium, niobium and antimony; Y is at least one element selected from the group consisting of lithium, sodium, potassium, rubidium, cesium and thallium; and n is the number of oxygen atoms sufficient to satisfy the valence requirements of the metallic elements, with the proviso that the sum of the atomic proportions of Fe, Co and/or Pb must range from 1 - 25.

2. The process according to claim 1, wherein the catalyst composition is represented by the formula, $$Mo_{12}Bi_{0.5-5}Me_{1-15}X_{0-5}Y_{0-3}O_n$$

wherein Me is iron, cobalt or lead and X, Y and n are the same as defined in claim 1.

3. The process according to claim 1, wherein X is antimony.

4. The process according to claim 1, wherein the catalyst composition is represented by the formula, $$Mo_{12}Bi_{0.5-5}Pb_{0.1-10}Co_{0.5-15}X_{0-5}Y_{0-3}O_n$$

wherein $1 \leq Pb + Co$ and X, Y and n are the same as defined in claim 1.

5. The process according to claim 1, wherein the catalyst composition is represented by the formula, $$Mo_{12}Bi_{0.5-5}Fe_{0.1-10}Pb_{0.1-10}X_{0-5}Y_{0+3}O_n$$

wherein $1 \leq Fe + Pb$ and X, Y and $n$ are the same as defined in claim 1.

6. The process according to claim 1, wherein the catalyst composition is represented by the formula, $$Mo_{12}Bi_{0.5-5}Fe_{1-10}Co_{0.5-15}X_{0-5}Y_{0+3}O_n$$

wherein X, Y and $n$ are the same as defined above.

7. The process according to claim 1, wherein the catalyst composition is represented by the formula, $$Mo_{12}Bi_{0.5+5}Fe_{1-10}Co_{2-10}Sb_{0.1-3}Y_{0-3}O_n$$

wherein Y and $n$ are the same as defined in claim 1.

8. The process according to claim 1, wherein the catalyst composition is represented by the formula, $$Mo_{12}Bi_1Fe_8Co_8Sb_1O_n$$

wherein $n$ is the same as defined in claim 1.

9. The process according to claim 1, wherein the catalyst composition is represented by the formula, $$Mo_{12}Bi_1Fe_8Co_8Sb_1K_{0.05}O_n$$

wherein $n$ is the same as defined in claim 1.

10. The process according to claim 1, wherein the reaction is carried out at 300° to 550° C.

11. The process according to claim 1, wherein the reaction is conducted under a pressure from slightly less than atmospheric to slightly more than atmospheric.

12. The process according to claim 1, wherein the oxygen is used in a proportion of 0.7 to 5 moles per mole of the 4-vinylcyclohexene.

13. The process according to claim 1, wherein the oxygen is used in a proportion of 1 to 3 moles per mole of the 4-vinylcyclohexene.

14. The process according to claim 1, wherein the molecular oxygen-containing gas is air.

15. The process according to claim 1, wherein the 4-vinylcyclohexene is diluted with a gas substantially inert to the reaction.

16. The process according to claim 15, wherein the inert gas is nitrogen, steam or saturated hydrocarbon.

17. The process according to claim 15, wherein the inert gas is steam.

18. The process according to claim 15, wherein the amount of the inert gas is at least 0.5 mole per mole of the 4-vinylcyclohexene.

* * * * *